United States Patent [19]

Wurster et al.

[11] 4,281,366
[45] Jul. 28, 1981

[54] LIGHTING SYSTEMS FOR SURGICAL OPERATIONS

[75] Inventors: Helmut Wurster, Oberderdingen; Ernst Blanc, Oberderdingen-Gross-Villars, both of Fed. Rep. of Germany

[73] Assignee: Richard Wolf GmbH, Knittlengen, Fed. Rep. of Germany

[21] Appl. No.: 124,075

[22] Filed: Feb. 25, 1980

[30] Foreign Application Priority Data

Mar. 8, 1979 [DE] Fed. Rep. of Germany ....... 7906381

[51] Int. Cl.³ ............................................. F21V 7/04
[52] U.S. Cl. ..................................... 362/32; 362/308; 362/309
[58] Field of Search .................. 362/32, 234, 33, 309, 362/308

[56] References Cited

U.S. PATENT DOCUMENTS

| 3,669,524 | 6/1972 | Shio | 362/32 |
| 3,772,506 | 11/1973 | Junginger | 362/32 |
| 4,128,332 | 12/1972 | Rowe | 362/32 |
| 4,206,495 | 6/1980 | McCaslin | 362/32 |

FOREIGN PATENT DOCUMENTS 832456 2/1952 Fed. Rep. of Germany ............ 362/32

*Primary Examiner*—Stephen J. Lechert, Jr.
*Attorney, Agent, or Firm*—Kinzer, Plyer, Dorn & McEachran

[57] ABSTRACT

This invention relates to lighting systems for use during surgical operations or examinations.

The device comprises a bundle of optical fibres having an intake area into which the light from an ellipsoidal mirror having a lamp therein can be beamed. A concave lens area located in an area facing away from the optical fibre bundle is co-axially situated forwardly adjacent the light intake area of the fibre bundle.

The concave area may be formed by grinding out portion of a transparent plate and the light from the mirror may be concentrated by an aspheric lens between the mirror lamp and the lens area.

5 Claims, 7 Drawing Figures

U.S. Patent    Jul. 28, 1981    4,281,366
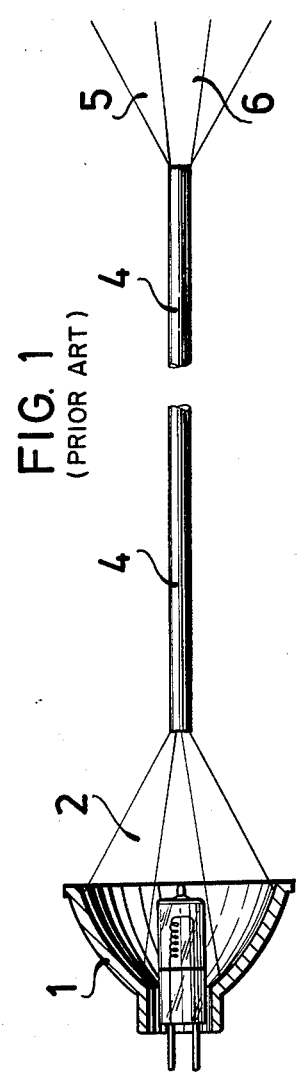
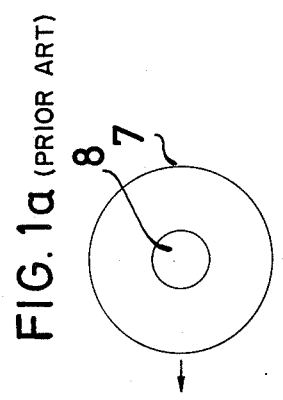
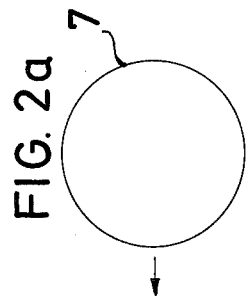
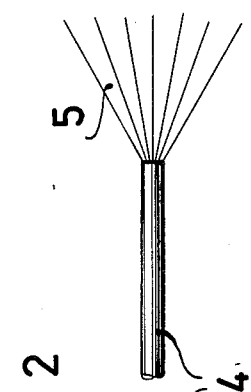
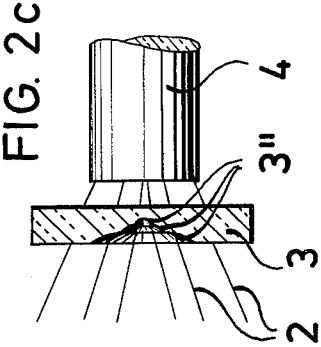
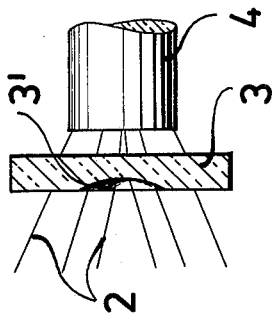
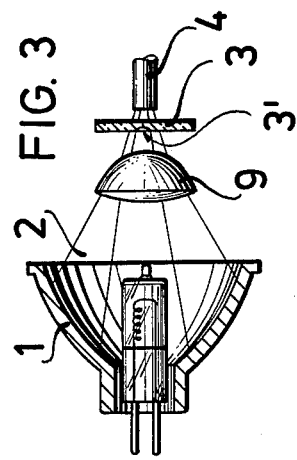

LIGHTING SYSTEMS FOR SURGICAL OPERATIONS

BACKGROUND OF THE INVENTION

In performing surgical operations, use is made, inter alia, of optical fibre bundles having a small intake area into which the light of an electrical lamp system, particularly a halogen bulb and a post-positioned condenser system or of an ellipsoidal mirror lamp is beamed, for illuminating sections to be examined and operated upon by the surgeon. The ellipsoidal mirror lamp displays the highest efficiency for these purposes, but has the disadvantage that a part of the light beam is shadowed by the bulb and that consequently none but inclined light rays are incident on the end faces of the fibres of the optical fibre bundle. This has the result that the field of illumination at the egress side of the optical fibre bundle has a dark spot in the central portion which obtrudes in very disturbing manner during examination and operation in the illuminated section.

It is therefore an object of the invention to retain the favourable efficiency of ellipsoidal mirror lamps but to minimise or even eliminate the darkening of the lighting field centre, hereinabove referred to.

SUMMARY OF THE INVENTION

Accordingly, the invention consists in a lighting system for surgical examinations and operations comprising an optical fibre bundle having an intake area into which the light of an ellipsoidal mirror lamp can be beamed, wherein a concave lens area located in the area facing away from said optical fibre bundle is co-axially situated forwardly adjacent said light intake area of said optical fibre bundle.

The light beams of the ellipsoidal mirror lamp emerging at an angle to the axis of the optical fibre bundle are deflected in the axial direction of the optical fibre bundle by the concave lens area which may be ground-into a small transparent e.g. glass, plate, and penetrate into the optical fibre bundle at right angles to the light intake or ingress area, i.e. the light distribution across the section which is to be illuminated is homogenised, so that the surgical area of the patient's body for examination or operation is illuminated in completely even manner. It will be understood that the radius of the concave lens area as well as its diameter, should be adapted to the refractive quotient of the lens and the diameter of the optical fibre bundle.

BRIEF DESCRIPTION OF THE DRAWINGS

In order that the invention may be more clearly understood, reference will now be made to the anexed drawings which show certain embodiments thereof by way of example and a prior art system for comparison purposes, and in which:

FIG. 1 diagrammatically and in sideview shows a known lighting system comprising an ellipsoidal mirror lamp with an optical fibre bundle, FIG. 1a shows the examination area produced the system of FIG. 1 in plan view, FIG. 2 shows a similar system except that it incorporates a concave lens area in accordance with the invention, FIG. 2a shows the homogenised examination section produced by the system of FIG. 2, FIGS. 2b and 2c show the part marked "x" in FIG. 2 in enlarged form of illustration with a different concave lens, and FIG. 3 shows a further embodiment representing a modification of the system shown in FIG. 2.

DETAILED DESCRIPTION OF PREFERRED EMBODIMENTS

Referring now to the drawings, a known priorart lighting system for illuminating a surgical section of a patient's body to be examined or operated on is shown in FIG. 1, and comprises an ellipsoidal mirror lamp 1 i.e. an electrical lamp, particularly a halogen (quartz-iodine) bulb built into a reflector (which may be dichroic), which beams its light 2 into the confronting end face of an optical fibre bundle 4 forming an intake or ingress area thereof, this light however emerging as a beam 5 with a dark central portion 6, the dark portion appearing as a dark spot in the illuminated examination area 7 as shown in FIG. 1a.

The avert this dark spot 8, which is very troublesome during an examination or operation, a concave lens area whose concave side is turned away from the end face of the optical fibre bundle, is joined e.g. by being adhered, to the light intake or ingress surface area of the optical fibre bundle 4, or positioned in direct contiguity in front of the light ingress surface, as shown in FIG. 2. According to the embodiment illustrated, this concave lens area is formed in that face of a small transparent plate, e.g. a small glass plate 3, which faces away from the optical fibre bundle 4. The area is formed by grinding a section co-axial with respect to the optical fibre bundle, the radius of said section being so selected as a function of the refractive index that the light beams otherwise incident at an angle on the beam reception surface of the optical fibre bundle from the ellipsoidal mirror lamp, are refracted and beamed at right angles into the beam reception surface of the light conductor 4. The surgical area 7 for examination which is to be illuminated is lit evenly as shown in FIG. 2a, and the light of the lamp 1 is homogenised in the area for examination. In this connection, the concave lens area 3' is selected to have a smaller diameter than the diameter of the optical fibre bundle 4, since light would otherwise be lost for the examination.

As shown in FIG. 2c, the concave lens area 3" may comprise several concentric annular concave lenses of different radius. Fibre bundles may consequently be applied, which have diameters adapted to these annular concave surfaces.

In another embodiment shown in FIG. 3, an aspheric lens 9 is located between the ellipsoidal mirror lamp 1 and the lens area 3' and the optical fibre bundle so as to concentrate the light onto the lens area.

The concave lens area need not be formed in a transparent plate but may in fact take the form of a discrete concave lens as will be apparent to those skilled in the art to which the invention relates. For this reason it is believed unnecessary to illustrate it.

We claim:

1. A lighting system for surgical examinations and comprising an optical fibre bundle having an intake area into which the light of an ellipsoidal mirror lamp can be beamed, wherein a concave lens area located in the area facing away from said optical fibre bundle is co-axially situated forwardly adjacent said light intake area of said optical fibre bundle.

2. A lighting system according to claim 1 wherein said concave lens area is part of a concave lens.

3. A lighting system according to claim 1 wherein said concave lens area is an area ground into a transparent plate.

4. A lighting system according to claim 3, wherein said concave lens area comprises several concentric concave ground sections of different radius.

5. A lighting system according to claim 4, wherein an aspheric lens acting as a condenser lens is interposed between said mirror lamp and said concave lens area, so as to increase the light density.

* * * * *